US005382679A

United States Patent [19]

Galzigna

[11] Patent Number: 5,382,679
[45] Date of Patent: Jan. 17, 1995

[54] PROCESS FOR THE PREPARATION OF GLUTATHIONE S-ACYL DERIVATIVES, COMPOUNDS OBTAINED FROM SAID PROCESS AND AN INTERMEDIATE USEFUL FOR THE PREPARATION THEREOF

[75] Inventor: Lauro Galzigna, Padua, Italy

[73] Assignee: Boehringer Mannheim Italia S.p.A., Milan, Italy

[21] Appl. No.: 958,344

[22] PCT Filed: Jun. 21, 1991

[86] PCT No.: PCT/EP91/01154

§ 371 Date: Feb. 10, 1993

§ Date: Feb. 10, 1993

[87] PCT Pub. No.: WO92/00320

PCT Pub. Date: Jan. 9, 1992

[30] Foreign Application Priority Data

Jun. 26, 1990 [IT] Italy .................... 20760 A/90

[51] Int. Cl.⁶ .................. C07C 321/04; C07C 321/06; A01N 43/06
[52] U.S. Cl. ..................... 560/16; 560/153; 514/533; 514/438; 514/547; 549/78
[58] Field of Search ............. 560/16, 153; 549/78; 514/533, 438, 547

[56] References Cited

PUBLICATIONS

Makriyannis, JACS 95(25), 8403–6 (1973).
Ferrero, J. Antibiot. 43(6), 684–91 (Jun. 1990).
Uotila, Biochemistry 22(20) 1973 3938.

*Primary Examiner*—José G. Dees
*Assistant Examiner*—Joseph M. Conrad
*Attorney, Agent, or Firm*—Nikaido Marmelstein Murray & Oram

[57] ABSTRACT

A selective and high yield process for S-acylating glutathione, comprising the eaction between glutathione and an acyl chloride or a carboxylic anhydride in trifluoroacetic acid is described.

7 Claims, No Drawings

PROCESS FOR THE PREPARATION OF GLUTATHIONE S-ACYL DERIVATIVES, COMPOUNDS OBTAINED FROM SAID PROCESS AND AN INTERMEDIATE USEFUL FOR THE PREPARATION THEREOF

The present invention relates to a process for the preparation of glutathione S-acyl derivatives and esters thereof, to novel derivatives obtained from said process. The invention also relates to pharmaceutical compositions containing said glutathione S-acyl derivatives as active ingredients.

In these last years glutathione (GSH) has given rise to an increasing interest for the potential therapeutic effects as well as for metabolism thereof and for derivatives therefrom. GSH N,S-acyl derivatives were described, for instance, in Japanese patent applications (see Chemical Abstracts 97-7222755S and 77-5493M.

Moreover, glutathione S-acyl derivatives, whose sensitivity to enzymatic hydrolysis by specific human liver-esterases was studied (Biochemistry, Vol. 12, No. 20, 1973, 3938–3943), have already been described. Glutathione S-acyl derivatives are stable in serum and glutathione itself is released by the action of specific liver esterases; this makes possible using said derivatives as glutathione "pro-drug".

The hitherto known methods for the selective acylation of glutathione thio group, without involving the free amino group, are suitable for small scale preparations such as laboratory ones, but not for large industrial applications. For instance, S-acetyl and S-butyrylglutathione have been prepared by reacting glutathione with thioacetic and thiobutyric acids in 40 and 20% yields, respectively (J. Biol. Chem. 1954, 206: 327–333). Also enzymatic methods are known to prepare glutathione S-acyl derivatives (J. Biol. Chem. 1951, 190:685). The above mentioned enzymatic methods are clearly useful only for laboratory-scale preparations.

It has now been found a method for the specific preparation of glutathione S-acyl derivatives in high yields, starting from low cost and easily available reagents such as acyl halides or acid anhydrides.

Particularly, the process of the invention consists in reacting glutathione or esters thereof with acyl halides or acid anhydrides in trifluoroacetic acid. The stoichiometric ratios are not particularly critical but at least two acyl halide equivalents per glutathione equivalent are preferably used. Under such conditions, the amino group is completely protected against protonation and the only nucleophilic group which can react with the acylating agent is the free thiol. When two equivalents of acylating agent are used, one equivalent acylates the —SH group according to the faster reaction, while the other one induces intramolecular dehydration of the glycine moiety and 4-(H-5oxo-1,3-oxazoline derivative of formula II is accordingly formed.

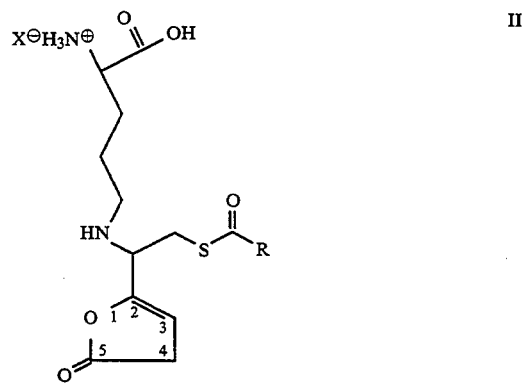

Such an intermediate of formula II shows a ketoenol equilibrium concerning positions 4 and 5.

The obtained S-acyl-glutathiones can be esterified according to conventional methods.

Some S-acyl-derivatives, which are prepared according to the invention are new, therefore they are a further object of the invention. Such derivatives can be used in human therapy, in the form of suitable pharmaceutical formulations, for the same already well-known applications of natural GSH. The only condition required is that the acyl residue can give rise in vivo to a non toxic, physiologically compatible carboxylic acid. Examples of such acids (deriving from the corresponding acyl residues) include acetic, propionic, pivalic, phenylacetic, benzoic, 2- or 3-thenoic acids.

The compounds of the invention can be formulated in pharmaceutical compositions suitable for oral or parenteral administrations, by using conventional techniques and excipients.

The following examples further illustrate the invention.

EXAMPLE 1

While stirring under nitrogen blanquet pivaloyl chloride (14.7 g) is dropwise added to a solution of L-glutathione reduced (18.4 g) in trifluoroacetic acid (200 ml) at room temperature.

The reaction mixture is heated to 40° C. and after about 20 minutes is treated with water (5 ml) and further heated at 40° C. for about 20 minutes. Then the solvent is removed under reduced pressure (40° C. 250 mmHg; 90° C. 20 mmHg) and the resulting oil is quenched with ethyl acetate (200 ml) leading to a white solid overnight. The crude precipitate is dissolved in warm (40° C.) acetone/water (5/1, 200 ml). After cooling in an ice-water bath for about two hours the white crystalline material formed is collected, washed with the solvent (30 ml) and dried over $CaCl_2$ under vacuum (40° C., 20 mmHg, 4 h) yielding γ-L-glutamyl-S-pivaloyl-L-cysteinyl-glycine (18,7 g, yield=80%).

(i) m.p. = 201°÷203° C.
(ii) $[\alpha]_D^{25} = -18$ $[\alpha]_{546}^{25} = -21.6$ (c=1 in $H_2O$)
(iii) TLC: $SiO_2$ $60F_{254}$, 0.25 thickness
eluent n-propanol:acetic acid:water = 10:1:5 (v/v)
eluition time: 45'
developing reagent: 0.5% ninhydrin is hereinafter referred to as NiN
Rf=0.53 (brown-red spot)
(iv) NMR Bruker 200 MHz: $DMSO_6$; δ (ppm), J(Hz)

| $^1H$ | | |
|---|---|---|
| 1.15 (9H, S) | | t-Bu |
| 1.90 (2H, m) | | Glu ($\beta$) |
| 2.30 (2H, m) | | Glu ($\gamma$) |
| 2.95 (1H, dd, $J_1 = 15$ $J_2 = 10$) | | Cys ($\beta$) |
| 3.30 (1H, dd, $J_1 = 15$ $J_2 = 5$) | | Cys ($\beta$) |
| 3.45 (1H, t, J = 7) | | Glu ($\alpha$) |
| 3.70 (2H, d, J = 5) | | Gly ($\alpha$) |
| 4.40 (1H, m) | | Cys ($\alpha$) |
| 8.42 (1H, d, = J = 7.5) | | Cys (NH) (exchangeable with $D_2O$) |
| 8.50 (1H, t, J = 5) | | Gly (NH) (exchangeable with $D_2O$) |

(v) Elemental analysis (for $C_{15}H_{25}N_3O_7S$)

| | C | H | N | S |
|---|---|---|---|---|
| Calculated (%) | 46.02 | 6.44 | 10.73 | 8.19 |
| Found (%) | 45.9 | 6.47 | 10.7 | 8.11 |

EXAMPLE 2

Using the procedure described in the Example 1 but with modified work-up, $\gamma$-L-glutamyl-S-pivaloyl-L-cystenyl glycine hydrochloride dihydrate can be obtained.

By reacting L-glutathione reduced (15.4 g) with pivaloyl chloride as previously outlined, the residual oil obtained from the reaction mixture concentrated under vacuum is dissolved in acetic acid (100 ml) under nitrogen. At room temperature hydrogen chloride in anhydrous diethyl ether (4.7N; 32 ml) is dropwise added to the resulting solution.

Under vigorous stirring more anhydrous diethyl ether (250 ml) is added to facilitate the crystallization of a white solid which is allowed to stand overnight under stirring. The precipitate is collected under nitrogen, washed with diethyl ether (50 ml) and dried over $P_2O_5$ (25° C. 10 mmHg 4 h). This leads to $\gamma$-L-glutamyl-S-pivaloyl-L-cysteinyl-glycine hydrochloride dihydrate (19 g; yield=89%)

(i) m.p.=90°÷100° C.
(ii) $[\alpha]_D^{25} = -12$ $[\alpha]_{546}^{25} = -14.3$ (c=1 MeOH)
(iii) Elemental analysis (as $C_{15}H_{25}N_3O_7S \cdot HCl \cdot H_2O$)

| | C | H | N | S |
|---|---|---|---|---|
| Calculated (%) | 46.02 | 6.44 | 10.73 | 8.19 |
| Found (%) | 45.9 | 6.47 | 10.7 | 8.11 |

(iv) NMR Bruker 200 MHz; DMSO-$d_6$: $\delta$ (ppm); J(Hz)

| | $^1H$ | | $^{13}C$ | |
|---|---|---|---|---|
| 1.15 | (9H, s) | | 27 | T-Bu |
| 2 | (2H, m) | | 26 | Glu ($\beta$) |
| 2.30 | (2H, m) | | 30 | Glu ($\gamma$) |
| 2.9 | (1H, dd, $J_1 = 15$, $J_2 = 10$) | | 30 | Cys ($\beta$) |
| 3.25 | (1H, dd, $J_1 = 15$, $J_2 = 5$) | | | Cys ($\beta$) |
| 3.7 | (2H, m) | | 40 | Gly ($\alpha$) |
| 3.85 | (1H, m) | | 51 | Glu ($\alpha$) |
| 4.4 | (1H, m) | | 51 | Cys ($\alpha$) |
| 8.35 | (1H, m) | | | Gly (NH) (exchangeable with $D_2O$) |
| 8.4 | (1H, d | | | Cys (NH) (exchangeable |

| | $^1H$ | | $^{13}C$ | |
|---|---|---|---|---|
| | | | | with $D_2O$) |

NMR Bruker 200 MHz, $D_2O$

| | $^1H$ | | | |
|---|---|---|---|---|
| 1.25 | (9H, S) | | | T-Bu |
| 2.2 | (2H pseudo q, J = 7) | | | Glu ($\beta$) |
| 2.56 | (2H, t, (J = 7) | | | Glu ( ) |
| 3.22 | (1H, dd, $J_1 = 14$, $J_2 = 8$) | | | Cys ($\beta$) |
| 3.45 | (1H, dd, $J_1 = 14$, $J_2 = 5$) | | | Cys ($\beta$) |
| 4.00 | (1H, t, J = 7) | | | Glu ( ) |
| 4.02 | (2H, s) | | | Gly ( ) |
| 4.65 | (1H, dd, $J_1 = 5$, $J_2 = 8$) | | | Cys ( ) |

EXAMPLE 3

Using in the procedure of Example 1 acetyl chloride, in place of pivaloyl chloride, L-glutathione reduced (15.4 g) provides, after usual work-up, a crude white solid which is dissolved in warm acetone/water (2/1; 40° C.; 300 ml). The obtained solution is further diluted with more acetone (100 ml) and cooled on ice-water bath. After about two hours the white crystalline precipitate is collected, washed with the solvent (40 ml) and dried under vacuum affording $\gamma$-L-glutamyl-S-acetyl-L-cysteinyl-glycine (14.8 g yield=85%)

(i) m.p.=202°÷204° C.
(ii) $[\alpha]_D^{25} = -27.5$ $[\alpha]_{546}^{25} = -32.6$ (c=1.1 $H_2O$)
(iii) TLC: $SiO_2$ 60$F_{254}$; 0.25 Thickness
eluent n-propanol: acetic acid: water=10:1:5 (V/V)
eluition time: 45'
developing reagent: NiN
Rf=0.37 (brown-red spot)
(iv) NMR Bruker 200 mHz; DMSO-$d_6$; $\delta$ (ppm) J(Hz)

| | $^1H$ | | |
|---|---|---|---|
| 1.95 | (2H, S) | | Glu ($\beta$) |
| 2.3 | (5H s + m) | | Glu ($\gamma$) + $\underline{CH_3}$ |
| 2.95 | (1H, dd, $J_1 = 15$, $J_2 = 10$) | | Cys ($\beta$) |
| 3.32 | (1H, dd, $J_1 = 15$, $J_2 = 5$) | | Cys ($\beta$) |
| 3.45 | (1H, t, J = 5) | | Glu ($\alpha$) |
| 3.7 | (2H, d, J = 5) | | Gly ($\alpha$) |
| 4.4 | (1H, m) | | Cys ($\alpha$) |
| 8.5 | (2H, d, J = 5) | | Cys (NH)-Gly(NH) |

(v) Elemental analysis (as $C_{12}H_{19}N_3O_7S$)

| | C | H | N | S |
|---|---|---|---|---|
| Calculated (%) | 41.25 | 5.48 | 12.03 | 9.18 |
| Found (%) | 41.29 | 5.51 | 12.05 | 9.09 |

EXAMPLE 4

Using in the procedure of Example 1 benzoyl chloride in place of pivaloyl chloride, L-glutathione reduced (15.4 g) affords a crude white solid which is suspended in boiling acetone/water (3/1; 400 ml) for thirty minutes. After cooling at room temperature the white precipitate is collected by filtration and washed with acetone (20 ml). Under vacuum drying yields $\gamma$-L-glutamyl-S-benzoyl-L-cysteinyl-glycine (16 g yield=78%).

(i) m.p.=213°÷215° C.
(ii) $[\alpha]_D^{25} = -12$ $[\alpha]_{546}^{25} = -15$ (c=0.67 DMSO)
(iii) Elemental analysis (as $C_{17}H_{21}N_3O_7S$)

|  | C | H | N | S |
| --- | --- | --- | --- | --- |
| Calculated (%) | 49.63 | 5.14 | 10.21 | 7.79 |
| Found (%) | 49.67 | 5.05 | 10.1 | 7.60 |

(iv) TLC SiO$_2$ 60F$_{254}$ 0.25 Thickness
eluent: n-propyl OH: AcOH: H$_2$O = 10:1:5 (V/V)
elution time = 45'
developing reagent = NiN
Rf = 0.52 (pink spot)
(v) NMR Bruker 200 MH$_z$, DMSO-d$_6$, δ (ppm) J(Hz)

| $^1H$ | | |
| --- | --- | --- |
| 1.9 | (2H, m) | Glu (β) |
| 2.32 | (2H, m) | Glu (γ) |
| 3.2 | (1H, dd, J$_1$ = 14, J$_2$ = 10) | Cys (β) |
| 3.4 | (1H, t, J = 7.5) | Glu (α) |
| 3.6 | (1H, dd, J$_1$ = 14, J$_2$ = 5) | Cys (β) |
| 3.75 | (2H, d, J = 5) | Gly (α) |
| 4.55 | (1H, m) | Cys (α) |
| 7.55 | (2H, t) | Aro-m,m' |
| 7.7 | (1H, t) | Aro-p |
| 7.9 | (2H, d) | Aro-o,o' |
| 8.55 | (1H, d J = 8) | Cys (NH) |
| 8.75 | (1H, t J = 5) | Gly (NH) |

EXAMPLE 5

Under nitrogen atmosphere, pivaloyl chloride (15.9 g) is dropwise added to a stirred solution of ethyl γ-L-glutamyl-L-cysteinyl-glycinate (10.9) in trifluoroacetic acid (220 ml) at room temperature. The reaction mixture is warmed to 40° C. and about fifteen minutes later is treated with water (2.5 ml) and then allowed to stand at 40° C. for further fifteen minutes.

The solvent is removed under vacuum (40° C. 250 mmHg; 90° C. 20 mmHg) and the oily residue is treated with ethyl ether/ethyl acetate (1/1 200 ml). The overnight stirring at room temperature gives a white precipitate which is filtered off, washed with the above solvent mixture (50 ml) and dried over CaCl$_2$ in vacuo (40° C. 20 mmHg 3 h).

This yields ethyl γ-L-glutamyl-S-pivaloyl-L-cysteinyl-glycinate (9.2 g yield = 67.5%)
(i) m.p. = 143° ÷ 145° C.
(ii) IR (KBr cm$^{-1}$) 1740, 1635, 1520, 1460, 1210
(iii) TLC SiO$_2$ 60F$_{254}$ 0.25 Thickness
eluent n-propanol: AcOH: H$_2$O = 10:1:5 (V/V)
elution time: 45'
developing reagent: NiN
Rf = 0.6 (brown spot)
(iv) NMR Bruker 200 MH$_z$, DMSO-d$_6$; δ (ppm); J(Hz)

| $^1H$ | | |
| --- | --- | --- |
| 1.12 (9H, s) | | t-Bu |
| 1.15 (3H, t, J = 7.5) | | CH$_2$CH$_3$ |
| 1,95 (2H, m) | | Glu (β) |
| 2.30 (2H, m) | | Glu (γ) |
| 2.95 (1H, dd) | | Cys (β) |
| 3.20 (1H, dd,) | | Cys (β) |
| 3.68 (1H, t) | | Glu (α) |
| 3.75 (2H, m) | | Gly (α) |
| 4.05 (2H, q, J = 7.5) | | CH$_2$—CH$_3$ |
| 4.40 (1H, m) | | Cys (α) |
| 8.30 (1H, d) | | Cys (NH) |
| 8.55 (1H, t) | | Gly (NH) |

(v) [α]$_D^{25}$ = −24.9 [α]$_{546}^{25}$ = −29.1 ((c = 1 MeOH)

EXAMPLE 6

Using in the procedure of Example 5 benzoyl chloride in place of pivaloyl chloride, ethyl γ-L-glutamyl-S-benzoyl-L-cysteinyl glycinate is obtained (70% yield).
(i) m.p. = 157° ÷ 159° C.
(ii) [α]$_D^{25}$ −25 [α]$_{546}^{25}$ −29 (c = 1; H$_2$O)
(iii) TLC SiO$_2$ 60F$_{254}$ 0.25 Thickness
eluent: n-P$_2$OH: AcOH: H$_2$O = 10:1:5
elution time: 45'
developing reagent: NiN
Rf = 0.61 (brown spot)
(iv) NHR bruker 200 MHz DMSO-d$_6$ δ (ppm) J(Hz)

| $^1H$ | | |
| --- | --- | --- |
| 1.15 | (3H, t, J = 8) | CH$_2$CH$_3$ |
| 2.00 | (2H, m) | Glu (β) |
| 2.35 | (2H, m) | Glu (γ) |
| 3.2 | (1H, dd) | Cys (β) |
| 3.55 | (1H, dd) | Cys (β) |
| 3.65 | (1H, m) | Glu (α) |
| 3.8 | (2H, d) | Gly (α) |
| 4.05 | (2H, d, J = 8) | C$\underline{H}_2$—CH$_3$ |
| 4.55 | (1H, m) | Cys (α) |
| 7.50-7.9 | (5H, t + t + d) | $\underline{H}$-Aro |
| 8.4 | (1H, d) | Cys (H) |
| 8.55 | 1H, t) | Gly (NH) |

EXAMPLE 7

Using in the procedure of example 5 acetyl chloride in place of pivaloyl chloride, ethyl γ-L-glutamyl-S-acetyl-L-cysteinyl glycinate is obtained (86.9% yield).
(i) m.p. = 130° ÷ 132° C.
(ii) [α]$_D^{25}$ −24.5 [α]$_{546}^{25}$ −28 (c = 1.03 in H$_2$O)
(iii) TLC SiO$_2$ 60F$_{254}$ 0.25 Thickness
eluent: nP$_2$OH; AcOH; H$_2$O = 10:1:5 (v/v)
elution time: 45'
developing reagent: 0.5% NiN
Rf = 0.55 (brown-red spot)
(iv) NMR Bruker 200 MHz DMSO-d$_6$ δ (ppm) J(Hz)

| $^1H$ | | |
| --- | --- | --- |
| 1.2 | (3H, t, J = 6) | —CH$_2$ C$\underline{H}_3$ |
| 1.9 | (2H, m) | Glu (β) |
| 2.3 | (5H, s + m) | Glu (γ) + C$\underline{H}_3$-H |
| 2.95 | (1H, d, d) | Cys (β) |
| 3.30 | (1H, d, d) | Cys (β) |
| 3.70 | (1H, t) | Glu (α) |
| 3.80 | (2H, d) | Gly (α) |
| 4.05 | (2H, q, J = 6) | —C$\underline{H}_2$CH$_3$ |
| 4.40 | (1H, m) | Cys (α) |
| 8.30 | (1H, d) | Cys (-NH) |
| 8.55 | (1H, t) | Gly (-NH) |

EXAMPLE 8

Following the procedure described in Example 3 but using two molar equivalents of acetic anhydride, instead of acetyl chloride, the same product γ-L-glutamyl-S-acetyl-L-cysteinyl-glycine is obtained. (67%) yield).

EXAMPLE 9

By using the same procedure described in Example 1 but reacting reduced glutathione (12.5 g) with an 1.2 molar excess of pivaloyl chloride (5.9 g) pure γ-L-glutamyl-S-pivaloyl-L-cysteinyl-glycine (11.3 g) is obtained. (71% yield)

EXAMPLE 10

Using in the procedure of example 1 phenylacetyl-chloride in place of pivaloyl-chloride, γ-L-glutamyl-S-phenylacetyl-L-cysteinyl-glycine is obtained (80% yield).

(i) m.p. = 195° ÷ 197° C.

(ii) $[\alpha]_D^{25} = -30.5$ $[\alpha]_{546}^D = -36$ (C=1.05—DMSO)

(iii) TLC SiO$_2$ 60F$_{254}$ 0.25 Thickness eluent : n-P$_2$OH; AcOH; H$_2$O = 10:1:5 (v/v)

elution time: 45' developing reagent: 0.5% NiN

Rf = 0.64 (brown-red spot)

(iv) NMR Bruker 200 MHz DMSOd$_6$ δ (ppm) J(Hz)

| $^1H$ | |
|---|---|
| 1.90 (2H, m) | Glu (β) |
| 2.30 (2H, m) | Glu (γ) |
| 2.95 (1H, d, d) | Cys (β) |
| 3.30 (1H, d, d) | Cys (β) |
| 3.45 (1H, t) | Glu (α) |
| 3.20 (2H, d) | Gly (α) |
| 3.10 (2H, s) | $CH_2—C_6H_5$ |
| 4.40 (1H, m) | Cys (α) |
| 7.27 (5H, m | $C_6H_5$ |
| 8.45 (1H, d) | Cys (-NH) |
| 8.55 (1H, t) | Gly (NH) |

Elemental analysis (as C$_{18}$H$_{23}$N$_3$O$_7$S)

| | C | H | N | S |
|---|---|---|---|---|
| Calculated (%) | 50.81 | 5.45 | 9.87 | 7.53 |
| Found (%) | 50.57 | 5.45 | 9.91 | 7.46 |

TABLE

The enzymatic hydrolysis specific activity of thioester bond is expressed as -SH released nmoles/min/mg of proteins. Tests with different concentrations of proteins and with different concentrations of substrate proved the enzymatic nature of the hydrolysis. Spontaneous hydrolysis of the substrates ranges from 1% to 10% maximum. The values are expressed as the mean ± SD on 6 tests.

| GSH derivative (0, 16 mM) | Cytosol | Serum | Ratio |
|---|---|---|---|
| S-acetyl | 10,8 ± 1,5 | 0 | 00 |
| S-pivaloyl | 6,9 ± 0,7 | 0 | 00 |
| S-phenylacetyl | 6,7 ± 0,9 | 0,05 ± 0,003 | 134,0 |
| S-benzoyl | 3,2 ± 1,1 | 0,04 ± 0,005 | 80,0 |
| S-thenoyl | 4,1 ± 1,0 | 0,06 ± 0,001 | 63,0 |
| S-benzoyl-diethyl-ester | 1,45 ± 0,8 | 0,07 ± 0,005 | 18,5 |
| S-benzoyl-monoethyl-ester | 0,6 ± 0,08 | 0,10 ± 0,004 | 6,0 |

As far as the ratio of intracellular to extracellular hydrolysis rate is concerned, the following scale can be established: S-acetyl > S-pivaloyl > S-phenylacetyl > S-benzoyl > S-thenoyl > S-benzoyl-diethylester > S-benzoyl-monoethylester.

I claim:

1. A process for the preparation of glutathione S-acyl derivatives, characterized in that glutathione or esters thereof are reacted with carboxylic acid anhydrides or with acyl halides in the presence of trifluoroacetic acid.

2. A process according to claim 1, characterized in that the ratio of acyl chloride equivalents to glutathione equivalent is least 2:1.

3. A process according to claim 2, wherein the acyl chloride is selected from acetyl, pivaloyl, phenacetyl, benzoyl, 2- or 3-thenoyl chlorides.

4. A process according to claim 1, characterized in that the acylating reaction is followed by hydrolysis with water to give S-acyl-glutathiones or esters thereof.

5. S-pivaloyl-glutathione derivative or S-thenoyl-glutathione derivative obtainable by the process as claimed in claim 1.

6. An S-acyl-glutathione selected from: S-pivaloyl-glutathione, and S-thenoyl-glutathione.

7. Pharmaceutical compositions containing an S-acyl-glutathione of claim 6 as active ingredient.

* * * * *